United States Patent
Bendek et al.

(10) Patent No.: US 10,398,839 B2
(45) Date of Patent: Sep. 3, 2019

(54) AUTOMATIC INJECTION DEVICE

(71) Applicant: SHL Medical AG, Zug (CH)

(72) Inventors: Antonio Bendek, Wellington, FL (US); Lucio Giambattista, Lighthouse Point, FL (US); John Laiosa, Lodi, NJ (US)

(73) Assignee: SHL Medical AG, Zug (CH)

( * ) Notice: Subject to any disclaimer, the term of this patent is extended or adjusted under 35 U.S.C. 154(b) by 0 days.

(21) Appl. No.: 15/118,429

(22) PCT Filed: Jan. 30, 2015

(86) PCT No.: PCT/EP2015/051889
§ 371 (c)(1),
(2) Date: Aug. 11, 2016

(87) PCT Pub. No.: WO2015/121080
PCT Pub. Date: Aug. 20, 2015

(65) Prior Publication Data
US 2017/0173264 A1    Jun. 22, 2017

(30) Foreign Application Priority Data
Feb. 14, 2014 (SE) ...................... 1450171

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31501* (2013.01); *A61M 5/31551* (2013.01);
(Continued)

(58) Field of Classification Search
CPC .......... A61M 5/31551; A61M 5/31561; A61M 5/31591; A61M 5/502; A61M 5/31595; A61M 5/31501; A61M 4/3156
See application file for complete search history.

(56) References Cited

U.S. PATENT DOCUMENTS 2,648,334 A * 8/1953 Brown .................... A61M 5/24
                                                                604/205
4,236,516 A * 12/1980 Nilson .................... A61J 1/062
                                                                604/214
(Continued)

FOREIGN PATENT DOCUMENTS

EP    3104909 A1    12/2016
TW    126612       1/1990
(Continued)

OTHER PUBLICATIONS

International Search Report and Written Opinion for Int. App. No. PCT/EP2015/051889, completed Jun. 26, 2015.

*Primary Examiner* — Emily L Schmidt
(74) *Attorney, Agent, or Firm* — McDonnell Boehnen Hulbert & Berghoff LLP

(57) ABSTRACT

The present invention relates to a medicament delivery device comprising a housing, which housing is arranged to accommodate a medicament container, which medicament container comprises a medicament delivery member; a power unit interactively connected to the housing comprises a force element and a plunger rod which is arranged to, upon activation, move linearly in the proximal direction and act on said medicament container for expelling a dose of medicament through said medicament delivery member; and a holding member connected to said power unit and to said container holder. The invention is characterized in that the plunger rod comprises at least one first guide-and-stop element configured to interact with at least one second guide-and-stop element on said a holding member for limiting the linear distance the plunger rod is capable of moving during expelling of medicament and which distance corresponds to a dose volume.

9 Claims, 15 Drawing Sheets

(52) U.S. Cl.
CPC ...... *A61M 5/31591* (2013.01); *A61M 5/3204* (2013.01); *A61M 2005/206* (2013.01); *A61M 2005/208* (2013.01); *A61M 2207/00* (2013.01)

(56) References Cited

U.S. PATENT DOCUMENTS

| | | | |
|---|---|---|---|
| 6,083,201 A * | 7/2000 | Skinkle | A61M 5/1454 604/118 |
| 6,562,006 B1 * | 5/2003 | Hjertman | A61M 5/31553 604/208 |
| 7,927,303 B2 | 4/2011 | Wyrick | |
| 2005/0101919 A1 | 5/2005 | Brunnberg | |
| 2008/0051715 A1 | 2/2008 | Young et al. | |
| 2012/0123350 A1 * | 5/2012 | Giambattista | A61M 5/2033 604/198 |
| 2012/0203184 A1 | 8/2012 | Selz et al. | |
| 2013/0102971 A1 | 4/2013 | Olson | |

FOREIGN PATENT DOCUMENTS

| | | |
|---|---|---|
| TW | 200628182 A | 8/2006 |
| TW | 201304828 A | 2/2013 |
| WO | 94/06494 A1 | 3/1994 |
| WO | 2006/079900 A2 | 8/2006 |
| WO | 2012/125133 A1 | 9/2012 |
| WO | 2013/154954 A1 | 10/2013 |

\* cited by examiner

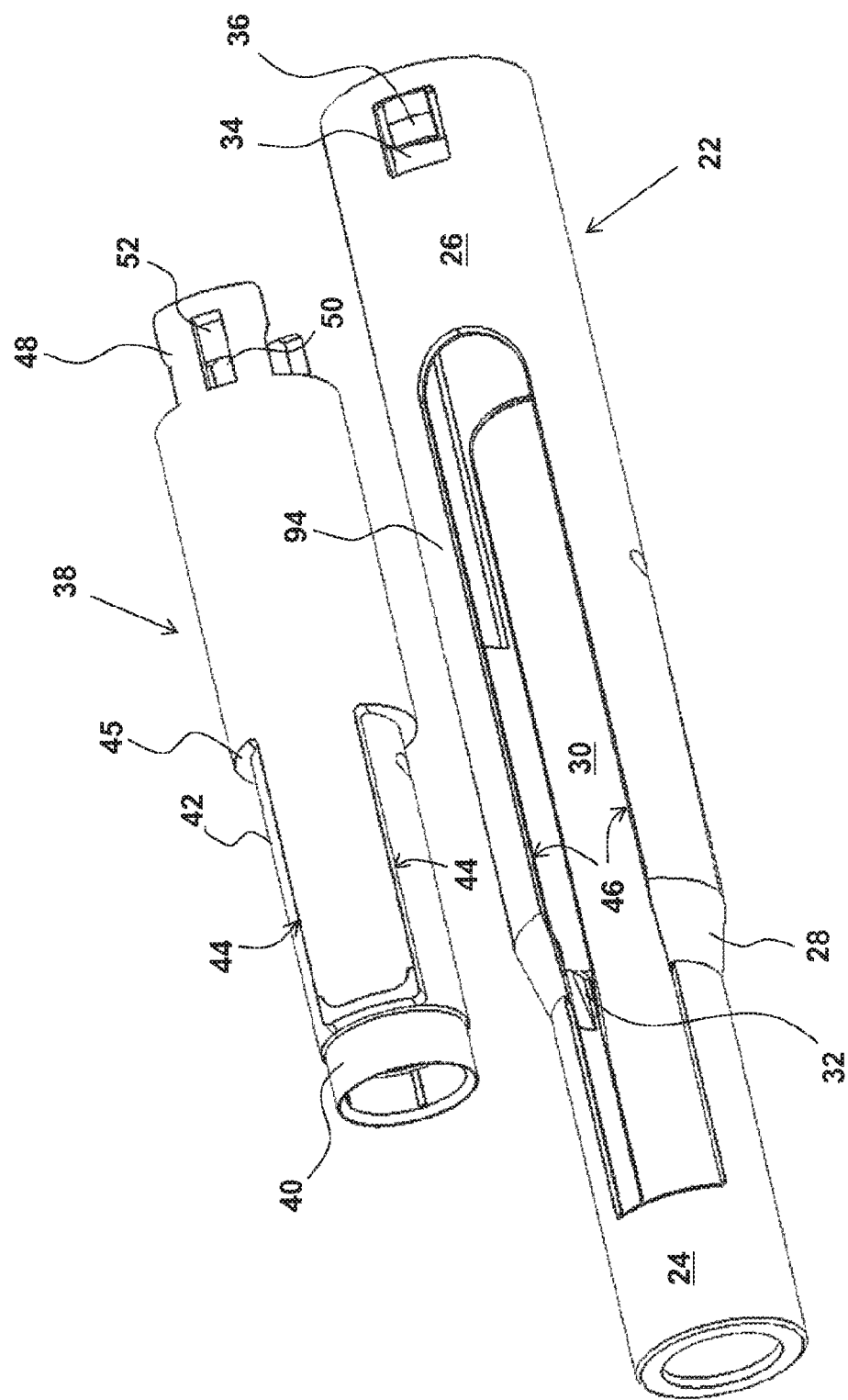

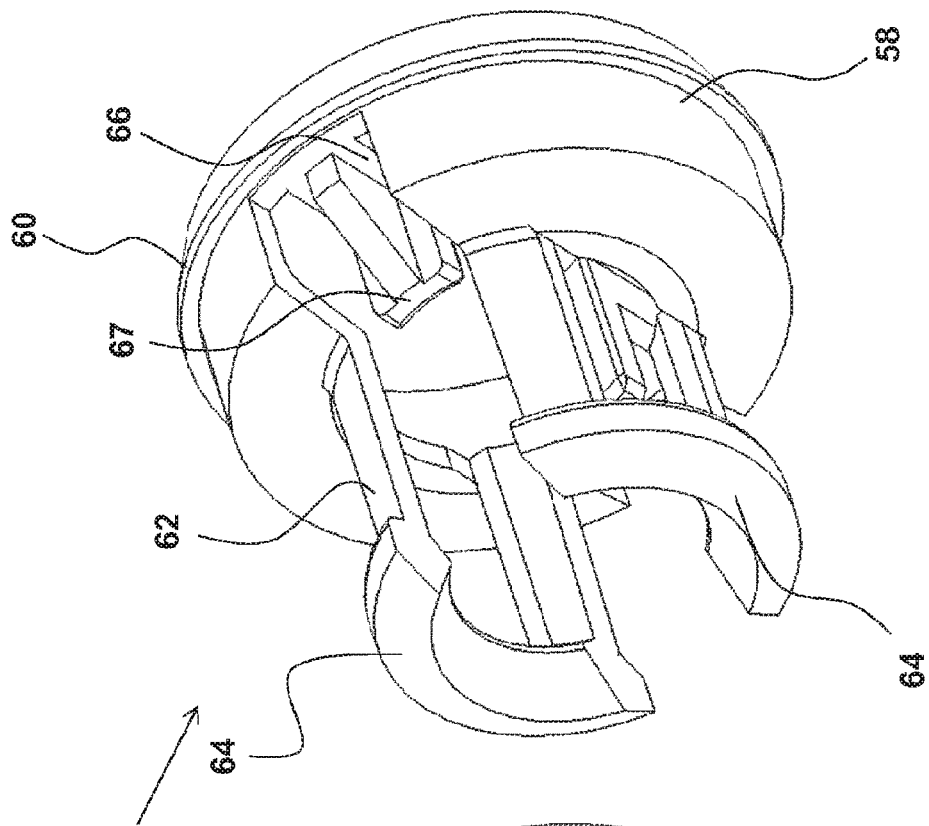
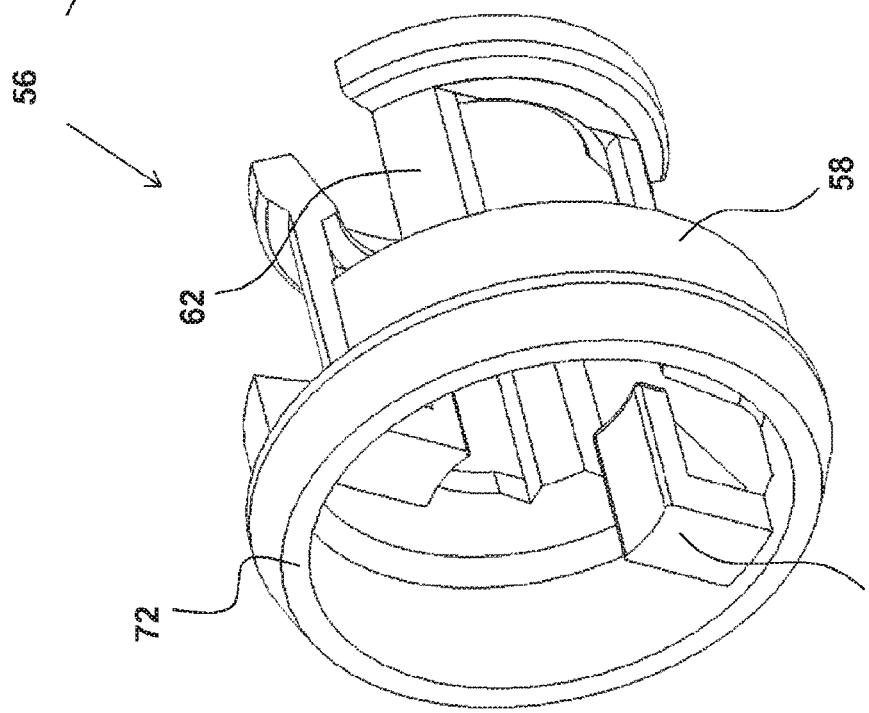
Fig. 4a
Fig. 4b

AUTOMATIC INJECTION DEVICE

CROSS REFERENCE TO RELATED APPLICATIONS

The present application is a U.S. National Phase Application pursuant to 35 U.S.C. § 371 of International Application No. PCT/EP2015/051889 filed Jan. 30, 2016, which claims priority to Swedish Patent Application No. 1450171-2 filed Feb. 14, 2014. The entire disclosure contents of these applications are herewith incorporated by reference into the present application.

TECHNICAL FIELD

The present invention relates to a medicament delivery device arranged to accommodate a medicament container of a certain size, and provided with a power pack operable to act on the medicament container for expelling doses of medicament.

BACKGROUND

There are a number of medicament delivery devices patented and/or on the market that comprise a number of functions. A specific medicament device is often designed to handle a certain prescribed medicament container having a certain dose volume.

In many cases, the whole volume is emptied when the device is utilised, i.e. a stopper is specifically arranged inside the tubular medicament container which moves to a proximal end position in the course of the medicament's delivery through a medicament delivery member. This means that the medicament containers are designed to contain a certain volume of medicament that is prescribed for treatment of patients. In many cases however, the prescribed volumes or doses may vary considerably depending on the patient and the condition of the ailment to be cured by the medicament. For example, children require a much lower dose than adults.

There are then usually two ways of handling this situation. When the medicament delivery device is designed to handle a certain container size, then the container has to be filled with different volumes of medicament according to the requirements of the patient. This implies that the stopper will be positioned at different locations inside the container. In order for this to work, the device has to be modified such that the drive mechanism acting on the stopper is able to handle the different start positions of the stopper when delivering the medicament.

Alternatively, one can handle the delivery of different doses by having some sort of dose setting mechanism, whereby the user or a physician is able to set the specific dose to be delivered. There are a multitude of devices that display this type of dose setting feature. A drawback with this solution is that the dose setting feature entails a number of additional components that are designed to interact, making the device more complicated and more expensive to manufacture.

A further way to handle the different dose sizes is to design the medicament delivery device to handle a particular medicament container size. This means that a specific design is produced for each dose size. This latter option is, however very costly and cannot be justified for most drugs. For this reason, this latter solution has not been developed to any extent.

There is thus room for improvements in this technical area of handling medicaments of different dose volumes to be delivered with a medicament delivery device.

SUMMARY

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The aim of the present invention is to remedy the drawbacks of the state of the art medicament delivery devices when handling different medicament volumes to be delivered to different patients.

This aim is obtained with a medicament delivery device according to the features of the independent patent claim. Preferable embodiments of the invention form the subject of the dependent patent claims.

The medicament delivery device may preferably comprise of a housing that can be gripped by a user when a dose of medicament is to be delivered. The housing may comprise of a number of housing parts that are inter-connectable with each other in suitable ways. The housing is arranged to accommodate a container holder with a medicament container which comprises of a medicament delivery member. The medicament delivery member may be an integral part of the container such as a syringe, or may be attachably arranged to the container, such as a separate injection needle connectable to a cartridge.

The housing may in one aspect be arranged to accommodate a certain size of the medicament container, as will be explained below. The device is preferably arranged with a power unit which is interactively connected to the housing and comprises of a force element and a plunger rod. The force element may be any suitable element capable of exerting a force when activated. The force element may thus be different types of springs, such as compression springs, torsion springs, gas springs and elastic elements, to mention a few. The force exerted may preferably be linear.

The force element is arranged and designed to act on the plunger rod. The plunger rod is in turn designed and arranged to move linearly in the proximal direction by the linear force from the force element when activated. The linear movement of the plunger rod will then cause it to act on the medicament container for expelling a dose of medicament through the medicament delivery member.

The device further comprises a holding member connected to said power unit and to said container holder.

According to one favourable feature, the plunger rod comprises at least one first guide-and-stop element configured to interact with at least one second guide-and-stop element on said a holding member for limiting the linear distance the plunger rod is capable of moving during expelling of medicament and which distance corresponds to a dose volume. The advantage with this solution is that the volume can be determined and also altered by choosing the linear distance the plunger rod can travel, when acting on a medicament container with a certain total volume.

According to one feasible solution, is that the at least one first guide-and-stop element is a longitudinally extending groove having a proximally directed stop surface and in that the at least one second guide-and-stop element is a radially inwardly positioned stop protrusion having a distally directed stop protrusion with a stop surface. The stop surfaces may then be positioned differently for different dose volumes in order to deliver the required dose volume.

According to one feasible solution, the at least one proximally directed stop surface on said plunger rod may be comprised in side surfaces of the at least one longitudinally extending groove arranged on said plunger rod. This provides thepossibility of altering the length of the groove in order to alter the dose volume to be delivered. It is thus a simple task to use plunger rods with different groove lengths when assembling the medicament delivery devices that are to deliver different dose volumes. The rest of the medicament delivery device, including the medicament container, remains unaltered.

According to a further aspect, said at least one distally directed stop protrusion is placed in said at least one longitudinally extending groove. The distally directed stop protrusion may then slide in the groove during dose delivery and will stop at an end position of the groove, i.e. where the stop surfaces meets, whereby the dose delivery sequence is terminated.

It is advantageous that the container holder is connected to the holding member since the container holder is arranged slidable in relation to said housing and thus it is operably connected to said power unit such that, upon activation, a penetration of said medicament delivery member is performed. Thus, further to provide a delivery sequence such as, an injection sequence, the medicament delivery device may also provide a penetration sequence when activated.

In order to further enhance the function of the medicament delivery device, it may comprise a medicament delivery member cover arranged slidable in relation to said housing, operably connected to the power unit such that it is movable to a shielding position of medicament delivery member after delivery such as, an injection needle after completed delivery e.g. injection. This feature minimizes the risk of accidental needle sticks after the device has been used. In order to further enhance the safety aspect, it may comprise a medicament delivery member cover locking mechanism capable of locking said medicament delivery member cover in the shielding position.

According to a further aspect, the holding member comprises of a ring-shaped body having an annular ledge arranged around its circumference, at least two distally directed members protruding from the ring shaped body and a ledge arranged between the two distally directed members; wherein the annular ledge is configured to interact with inwardly inclined tongues on distally directed tongues of the container holder for connecting the holding member to the container holder. Furthermore, the ledge of the holding member is arranged and shaped to fit into a circumferential groove of the plunger rod for connecting the holding member to the power unit.

According to another aspect, the power unit further comprises an actuator partially surrounding the plunger rod, an actuator sleeve coaxially and slidably arranged on the actuator, a compression spring arranged between the actuator sleeve and the housing and also a push button connected to the actuator; wherein the actuator comprises flexible tongues with inclined transition surfaces which meets with a band-shaped part with enlarged diameter and an annular inwardly directed ledge which fit into the circumferential groove of the plunger rod together with the ledges of the holding member, at least one stop ledges directed radially outwards from its outer surface and an attachment post for the push button; and wherein the actuator sleeve comprises a front end with a conical part ending in a ledge on its outer surface, a first annular ring, a second annular ring, two oppositely arranged cut-outs configured to accommodate the stop ledges.

According to yet another aspect, the medicament delivery member cover is operably connected to said power unit through flexible tongues that pass through the annular ledge of the actuator sleeve.

According to a further aspect, the container holder is arranged inside and coaxial with the medicament delivery member cover.

These and other aspects and advantages of the present invention will be apparent from the following detailed description of the invention and from the appending drawings.

BRIEF DESCRIPTION OF DRAWINGS

In the following detailed description of the invention, reference will be made to the accompanying drawings, of which

DETAILED DESCRIPTION

Figure 1:
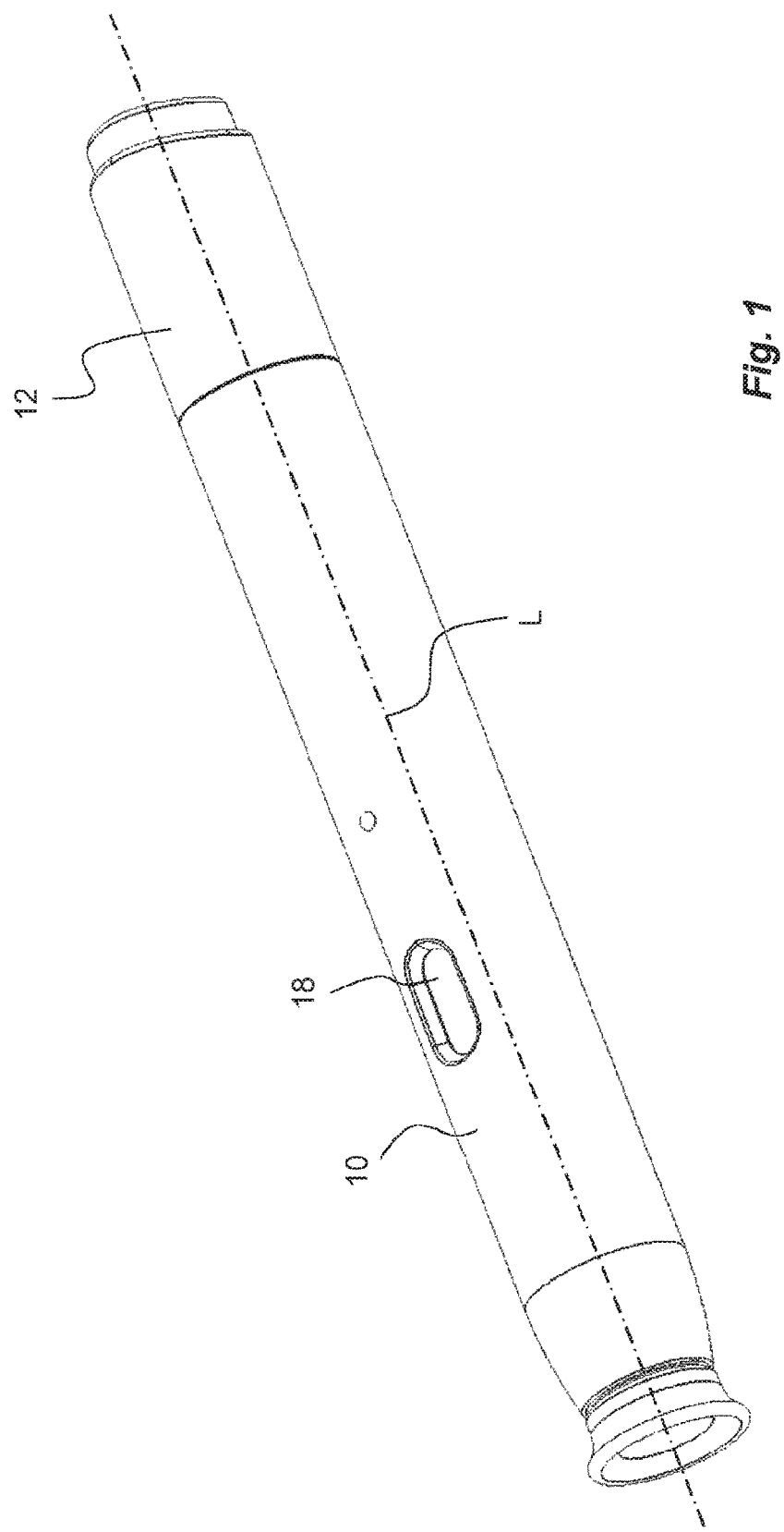
FIG. 1 is a perspective view of a medicament delivery device according to the invention.

The embodiment shown in the drawings comprises housing, more particularly a generally tubular proximal housing part 10 and a generally tubular distal housing part 12, FIG. 1. The housing parts are arranged with attachment elements for connecting the housing parts to each other. In the embodiment shown the attachment elements comprise circumferential grooves 14, FIG. 2, on an inner surface of a distal area of the proximal housing part 10 inter-connecting with circumferential ridges 16 on an outer surface of a proximal area of the distal housing part 12. It is however to be understood that other types of attachment elements may be utilized, such as threads, bayonet connections snap-in connectors to mention a few.

Figure 2:
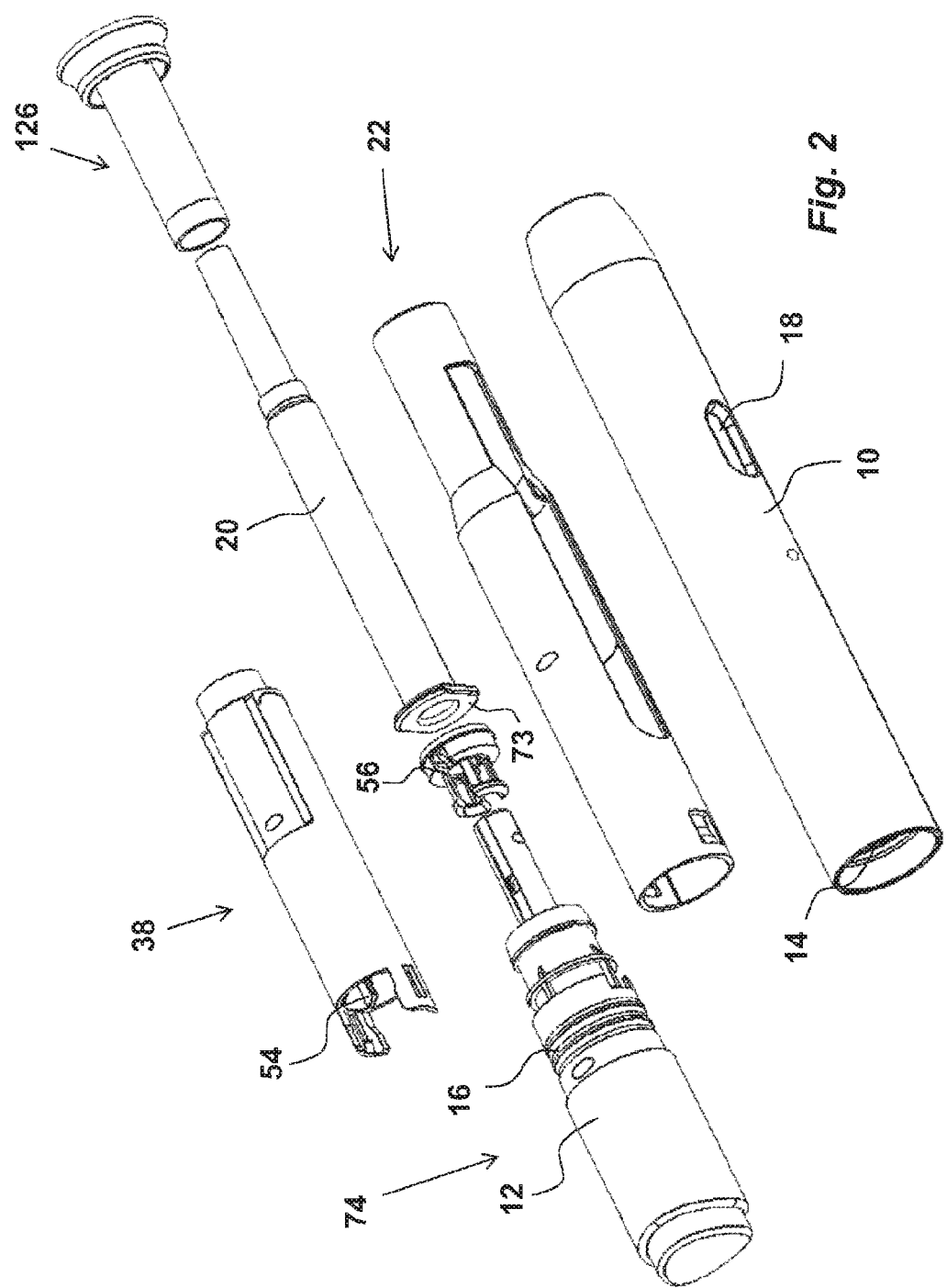
FIG. 2 is an exploded view of the device of FIG. 1, FIGS. 3-7 are detailed views of components comprised in the device of FIG. 1, and FIGS. 8-15 are cross-sectional views of the device of FIG. 1 in different functional positions.
Figure 5:
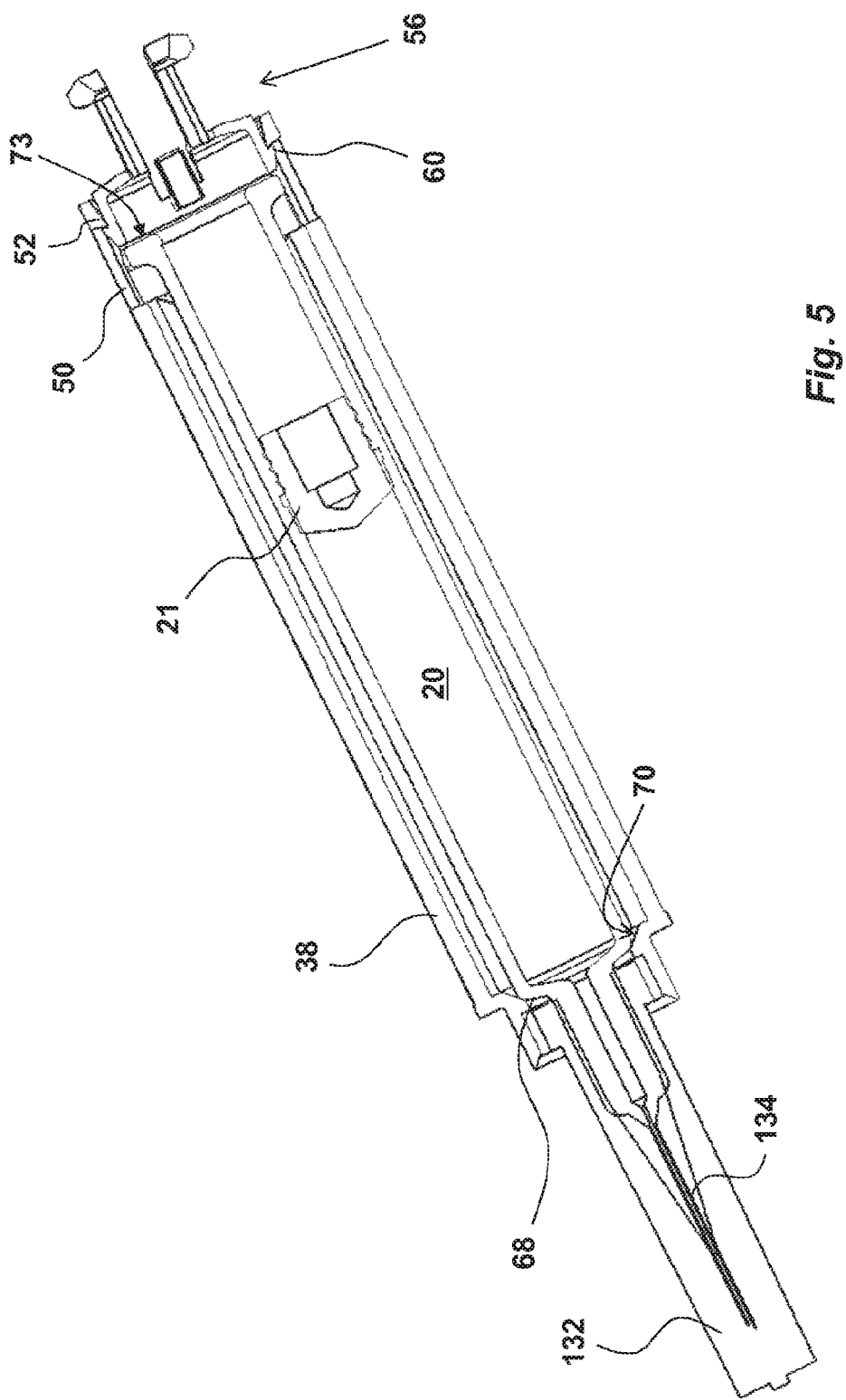

The proximal housing part 10 is arranged with openings or windows 18 for viewing a medicament container 20, FIG. 2, and has a somewhat narrowing proximal end. The medicament container is generally tubular and preferably made of a transparent material such as glass or clear plastic. A stopper 21, FIG. 5, is arranged movable inside the medicament container body. Inside the proximal housing part 10, a medicament delivery member cover 22 is slidably arranged, FIGS. 2 and 3. The medicament delivery member cover 22 is generally tubular provided with a first proximal part 24 having a certain diameter and a second distal part 26 having a diameter larger than the proximal part, where these parts are joined by an intermediate conical part 28, FIG. 3. Two elongated openings or windows 30 are arranged along the medicament delivery member cover 22, on opposite sides of the medicament delivery member cover 22, also for viewing the medicament container 20. On the inner surface of the conical part 28, a distally directed ledge 32 is arranged, FIG. 3. At the distal end of the medicament delivery member cover 22 two openings 34 are arranged opposite each other, where each opening is arranged with somewhat inwardly projecting, flexible, tongues 36, FIG. 3.

Furthermore, a container holder 38, FIGS. 3 and 5, is arranged inside and coaxial with the medicament delivery member cover 22, in the form of a generally tubular body. The proximal part of the container holder 38 is arranged with a neck portion 40 of lesser diameter. Adjacent to the neck portion 40 cut-outs 42 have been made on either side to form laterally directed guide surfaces 44 and proximally directed stop surfaces 45. These guide surfaces 44 cooperate with side surfaces 46 of the window 30 of the medicament delivery member cover 22, creating a rotational lock between the two components while allowing relative longitudinal movement of the medicament delivery member cover 22 relative to the container holder 38. The distal end of the container holder 38 is arranged with two distally directed tongues 48, where each tongue 48 is arranged with an opening 50 and an inwardly inclined tongue 52 on the distal edge of each opening 50. The container holder 38 is further arranged with radially directed flanges 54, FIG. 2, on its inner surface in order to obtain a space between the inner wall of the container holder and the medicament container 20 to be placed inside the container holder 38.

Figure 6:
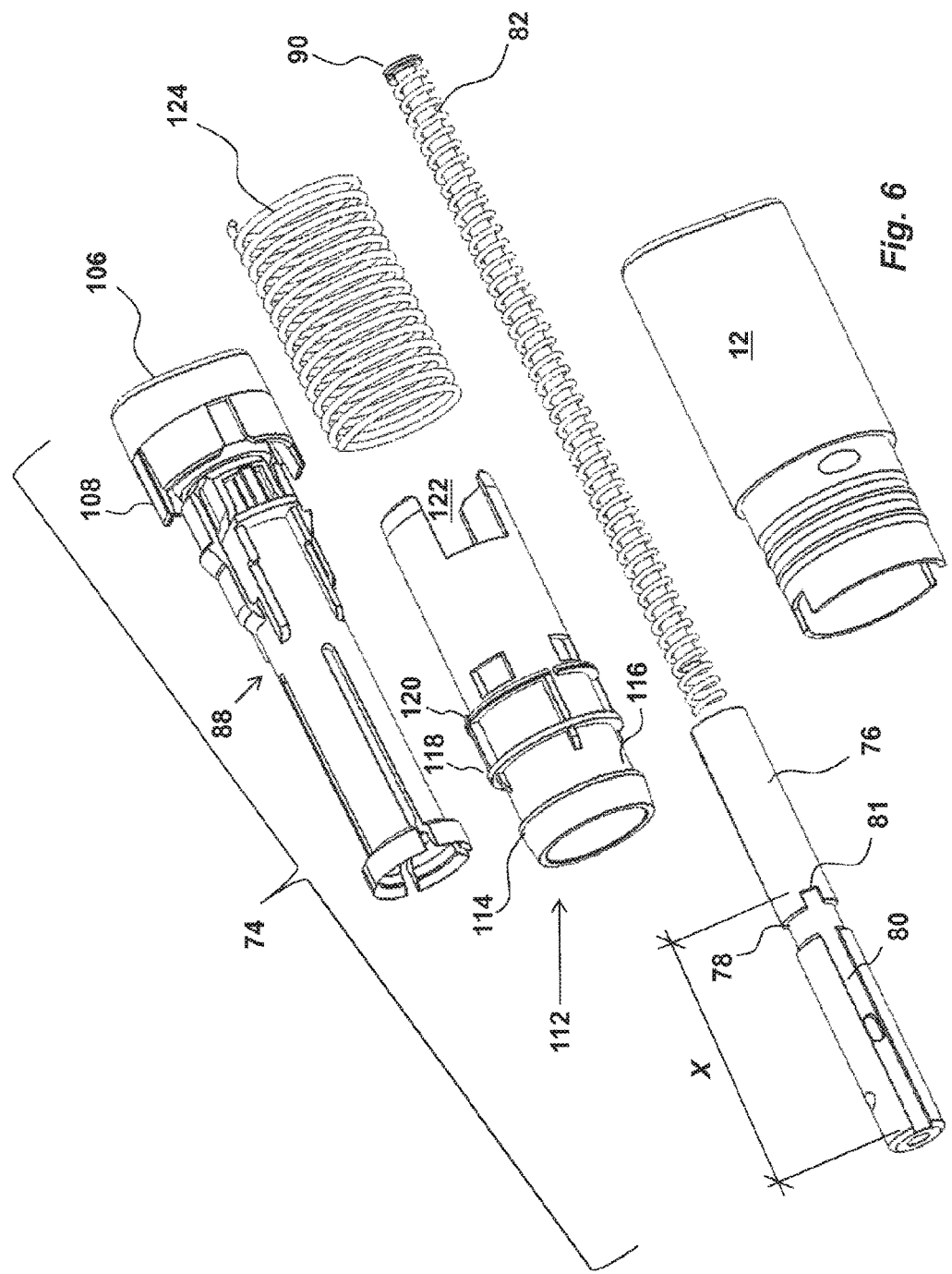

A power unit 74, FIGS. 2 and 6, is interactively connected to the housing and said power unit comprises a force element 82 and a plunger rod 76 which is arranged to, upon activation, move linearly in the proximal direction and act on said medicament container 20 for expelling a dose of medicament through said medicament delivery member 134.

Furthermore, a holding member 56 is provided, FIGS. 4a, 4b and 5 which is connected to the power unit and to the container holder. The plunger rod 76 comprises at least one first guide-and-stop element configured to interact with at least one second guide-and-stop element on said a holding member for limiting the linear distance the plunger rod is capable of moving during expelling of medicament and which distance corresponds to a dose volume.

The at least one first guide-and-stop element is a longitudinally extending groove 80 having a proximally directed stop surface 81 and the at least one second guide-and-stop element is a radially inwardly positioned stop protrusion 66, FIG. 4a having a distally directed stop protrusion 67 with a stop surface, FIG. 4b, the function of which will be described below.

The longitudinally extending grooves 80 are arranged on the outer surface of the plunger rod, extending from a proximal end of the plunger rod a certain length X in the distal direction and terminating in the proximally directed stop surface 81. The stop ledges 66 distally directed stop protrusions 67 with the stop surfaces of the holding member 56 are designed and arranged to fit into these grooves 80.

As seen in the embodiment of FIGS. 4a and 4b, the holding member 56 further comprises, a ring-shaped body 58, having an annular ledge 60 arranged around its circumference and four distally directed members 62 protruding from the ring shaped body 58 forming two pairs/sets of distally directed members 62 and wherein each pair is interconnected by a ledge 64 shaped as a circle segment. The holding member 56 is intended to cooperate with the container holder 38 to hold a medicament container in a firm position. As seen in FIG. 5, when a medicament container 20 is placed inside the container holder 38 by inserting it from a distal end of the container holder 38, a proximally directed shoulder 68 of the medicament container 20 is resting against a somewhat inclined annular support surface 70 of the container holder 38. The holding member 56 is then pushed into the distal end of the holding member 56 such that the annular ledge 60 passes the inclined tongues 52, locking the holding member 56 in the distal direction and wherein a proximal surface 72 of the holding member, FIG. 4a, is resting against a distally directed end surface 73 of the medicament container 20. The medicament container 20 is now held firmly in the longitudinal direction L between the support surface 70 and the proximal surface 72.

Furthermore, the plunger rod 76 is formed as a tube with an outer diameter somewhat smaller than the inner diameter of the medicament container body to be used. The plunger rod 76 is arranged with a circumferential groove 78 with a certain width, wherein the ledges 64 of the holding member 56 are arranged and shaped as to fit into the groove 78.

Figure 7:
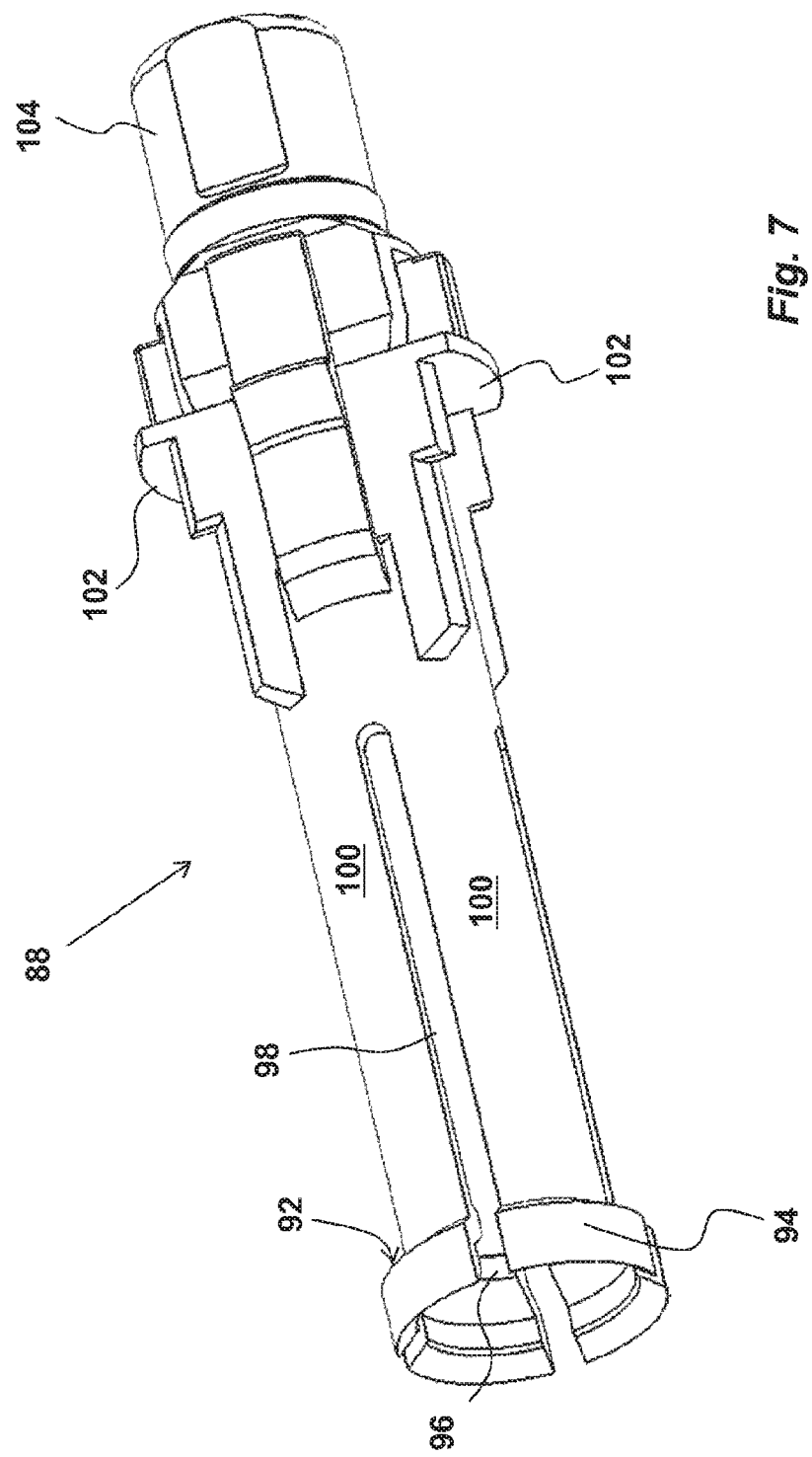

The power unit further comprises an actuator 88 with a mainly tubular shape, FIGS. 6 and 7, and partially surrounding the plunger rod, an actuator sleeve 112 coaxially and slidably arranged on the actuator 88, a compression spring 124 arranged between the actuator sleeve and the housing and a push button 106 connected to the actuator.

According to one embodiment, inside the plunger rod 76 a helical compression spring 82 is arranged between a proximal end wall 84 of the plunger rod 76 and a proximally directed end wall 86 of the actuator 88, FIG. 8, which will be described in more details below. Inside the spring 82 a spring guide 90 is placed.

A number of longitudinally directed cut-outs 98, FIG. 7, are arranged at the proximal part of the actuator 88 so as to form flexible tongues 100. At its proximal end, each flexible tongue 100 comprises inclined transition surfaces 92, which meets with a band-shaped part 94 with enlarged diameter and an annular inwardly directed ledge 96 which fit into the circumferential groove 78 of the plunger rod together with the ledges 64 of the holding member, as seen in FIG. 8. The actuator 88 is further provided with two stop ledges 102, which are directed radially outwards from the outer surface on either side. The distal end of the actuator 88 is arranged with an attachment post 104 for the push button 106, FIG. 6. The push button 106 is arranged with proximally directed tongues 108, FIGS. 6 and 8, where the tongues are interacting with inwardly arranged ledges 110 of the distal housing part 12, FIG. 1.

Figure 8:
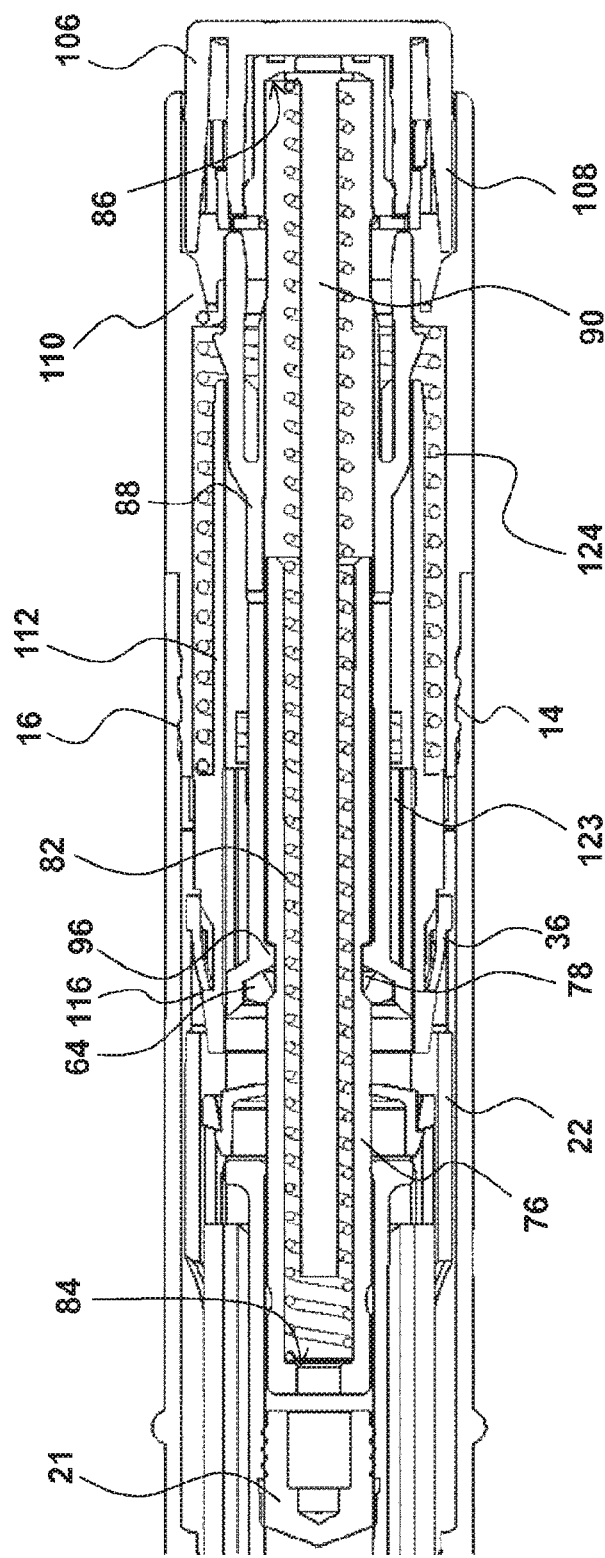

Coaxially outside the actuator 88, the actuator sleeve 112 is slidably arranged, FIGS. 6 and 8, also of a generally tubular form. It comprises a front end with a conical part 114 ending in a ledge 116 on its outer surface. At a distance from the ledge 116, a first annular ring 118 is arranged on the outer surface. A second annular ring 120 is also arranged a further distance from the ledge 116. The distal end of the actuator sleeve 112 is arranged with two oppositely arranged cut-outs 122 of a generally rectangular shape where the widths correspond to the width of the stop ledges 102 of the actuator 88. Longitudinally extending ribs 123, FIG. 8, comprised in a medicament delivery member cover locking mechanism, are arranged on the inner surface of the actuator sleeve 112, the function of which will be described below. The compression spring 124, hereafter named medicament delivery member cover spring, is surrounding the actuator 88, as seen in FIG. 8.

Figure 9:
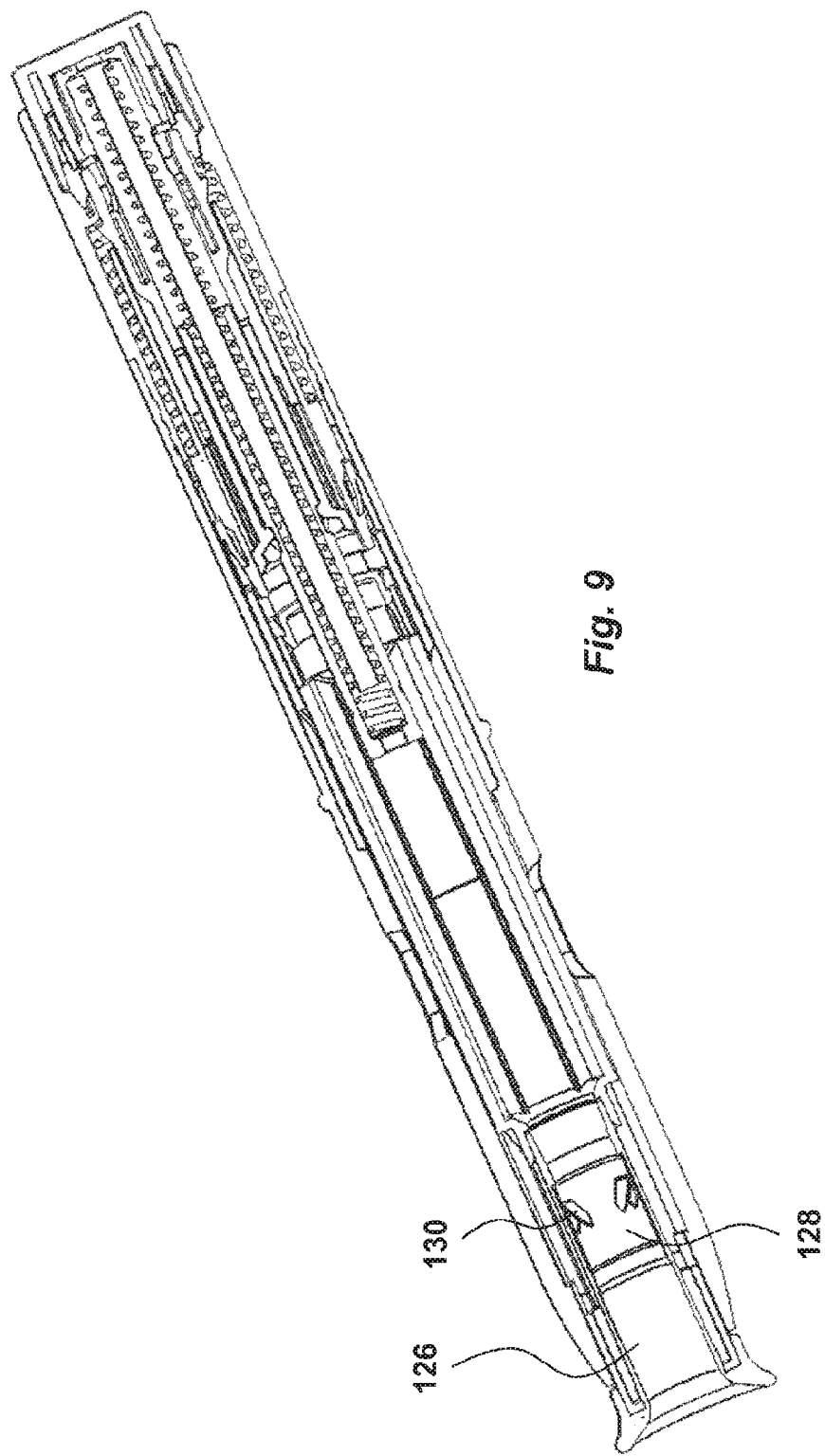

At the proximal end of the proximal housing part 10, a needle protection cap grabber 126 is arranged, FIGS. 2 and 9, having a generally tubular shape. It is inserted into the proximal part of the medicament delivery member cover 22 and held there by friction. Inside the cap grabber 126, a metal ring 128, FIG. 9, is arranged with sharp pointed tongues 130 directed somewhat inwards and towards the proximal end, designed and intended to grip into a medicament delivery member sheath 132, FIG. 5, surrounding and protecting a medicament delivery member 134, such as, an injection needle 134 of the medicament container 20.

The device is designed to function as follows: When the device is prepared before delivering it to an intended user, the proximal part of the device is assembled with a medicament container 20. The medicament container is thus placed in the container holder 38 from the distal end thereof, where the container holder 38 preferably is held such that the medicament container slides into the container holder until the proximally directed shoulder 68 of the medicament container 20 comes in contact with the support surface 70 of the medicament container. The container holder 38 in turn is placed into the medicament delivery member cover 22 with its guide surfaces 44 in contact with the side surfaces 46 of the cut-outs 30 of the medicament delivery member cover 22. Then this assembly is placed in the proximal housing part 10 from a distal direction.

The power unit 74 is assembled separately from the proximal part. The compression spring 82 is tensioned in that the plunger rod 76 is pushed into the actuator 88 in the distal direction until the inwardly directed ledges 96 of the tongues 100 of the actuator 88 are situated in the groove 78 of the plunger rod 76, FIG. 8. The actuator 88 with the plunger rod 76 is then pushed into the actuator sleeve 112 in the distal direction, which prevents the tongues 100 from moving outwards. Furthermore, the ledges 64 of the holding member 56 are also arranged in the groove 78, as seen in FIG. 8. The assembled components are then pushed into the distal housing part 12 from a proximal direction. Then a push button 106 is connected to the attachment post 104 of the actuator 88.

The power unit 74 is now connected to the distal end of the proximal housing part with its assembled components as described above. This causes the annular ledge 60 of the holding member 56 to pass the inwardly directed tongues 52 of the container holder, whereby the medicament container now is locked firmly. Further, the flexible tongues 36 of the medicament delivery member cover 22 pass the annular ledge 116 of the actuator sleeve 112, locking the two components together, FIG. 8. Lastly the grooves 14 on the proximal housing part 10 will engage with the ridges 16 of the distal housing part 12, FIG. 8, locking the two housing parts together. The medicament delivery member protection cap grabber 126 is inserted into the proximal end of the device. The device is now ready for use.

Figure 10:
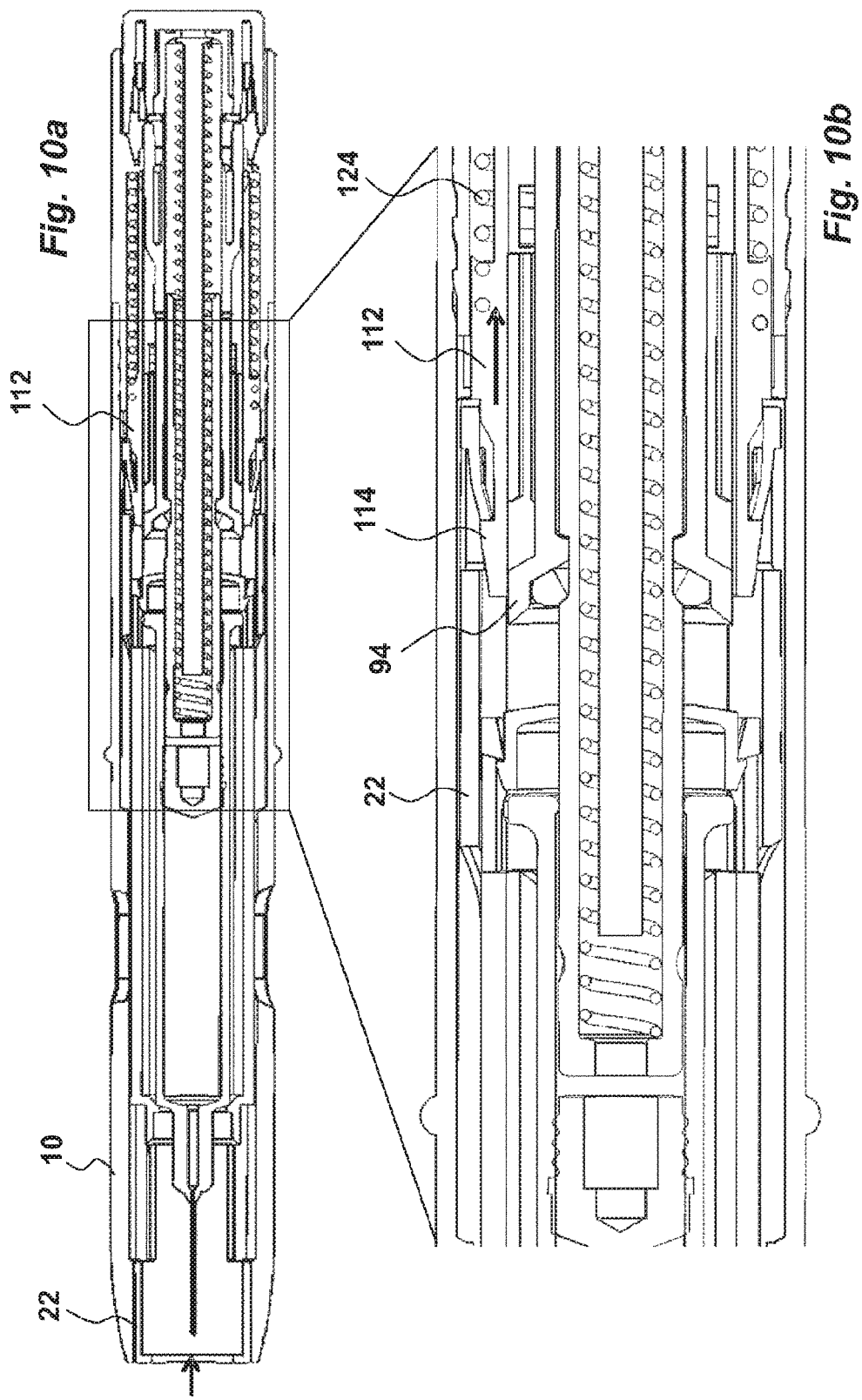

When a delivery as e.g. an injection is to be performed, the medicament delivery member protection cap grabber 126 is pulled in the proximal direction out of the proximal end of the device. This causes the sharp pointed tongues 130 to be pushed into the rubber medicament delivery member sheath 132 and to remove it from the medicament delivery member 134. The proximal end of the device can then be pressed against the delivery site and the somewhat projecting proximal end of the medicament delivery member cover 22 is pushed into the housing, FIG. 10a, against the force of the medicament delivery member cover spring 124 acting between the second annular ring 120 of the actuator sleeve 112 and a fixed support surface inside the distal housing part 12. The distally directed end surface of the medicament delivery member cover 22 is in contact with the first annular ring 118 of the actuator sleeve 112 and the movement in the distal direction of the medicament delivery member cover 22 causes the actuator sleeve 112 to move in the distal direction, whereby a part of the band-shaped part 94 will be placed outside the conical part 114 of the actuator sleeve 112, as seen in FIG. 10b.

Figure 11:
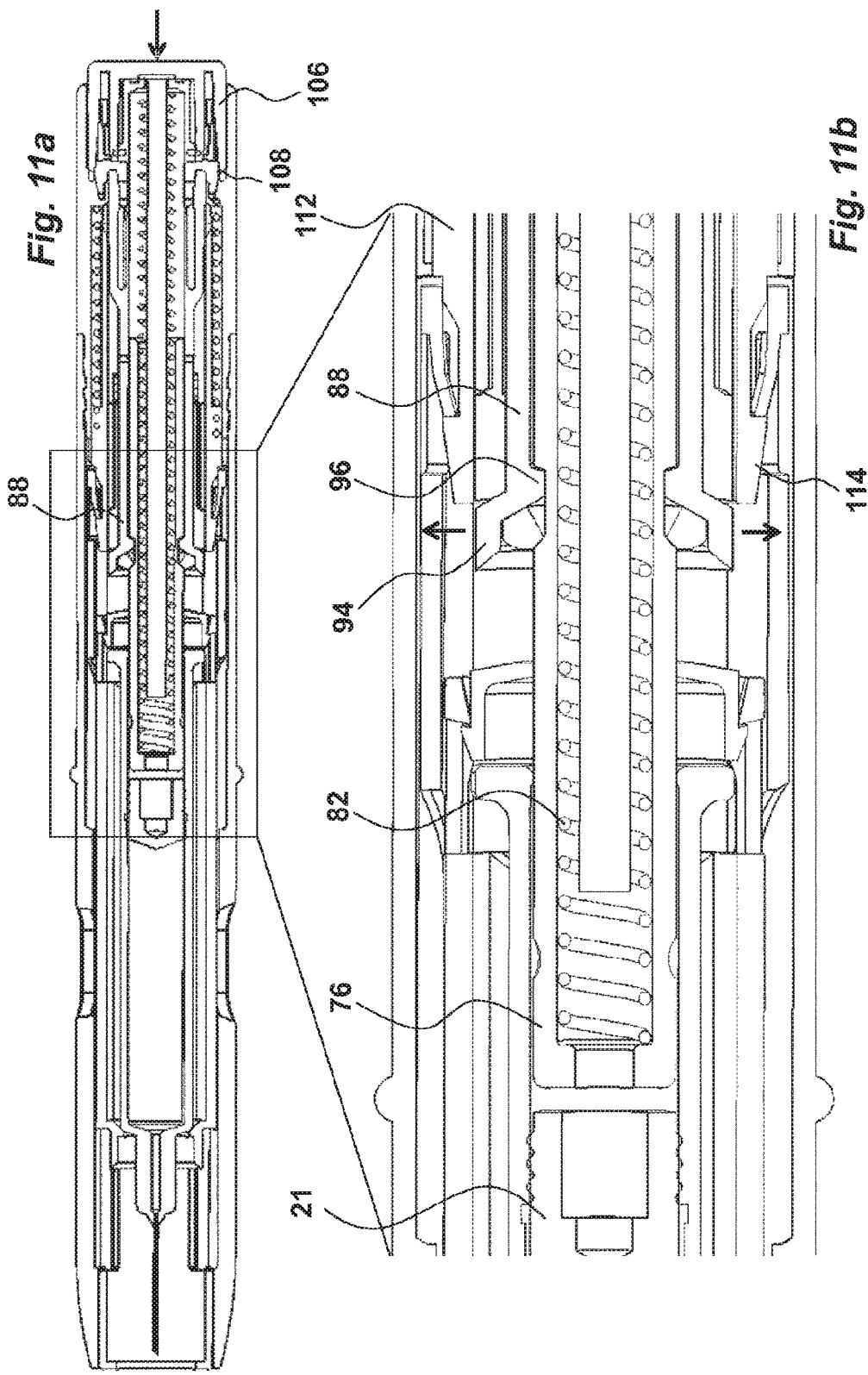

When activating the penetration and delivery e.g. injection, the user merely presses the push button 106, FIG. 11a. The proximally directed tongues 108 of the push button 106 then act against the ledges 110 of the inner surface, creating an initial resistance of the button, which then is overcome when the tongues 108 flex inwards as the button is moved inside the distal housing part. This causes the actuator 88 to be moved in the proximal direction whereby the band-shaped part 94 is moved completely out of the actuator sleeve 112, FIG. 11b. The resilient properties of the tongues 100 of the actuator 88 cause the ledges 96 to move out of the groove 78 of the plunger rod 76, which then is free to move due to the spring 82.

Figure 12:
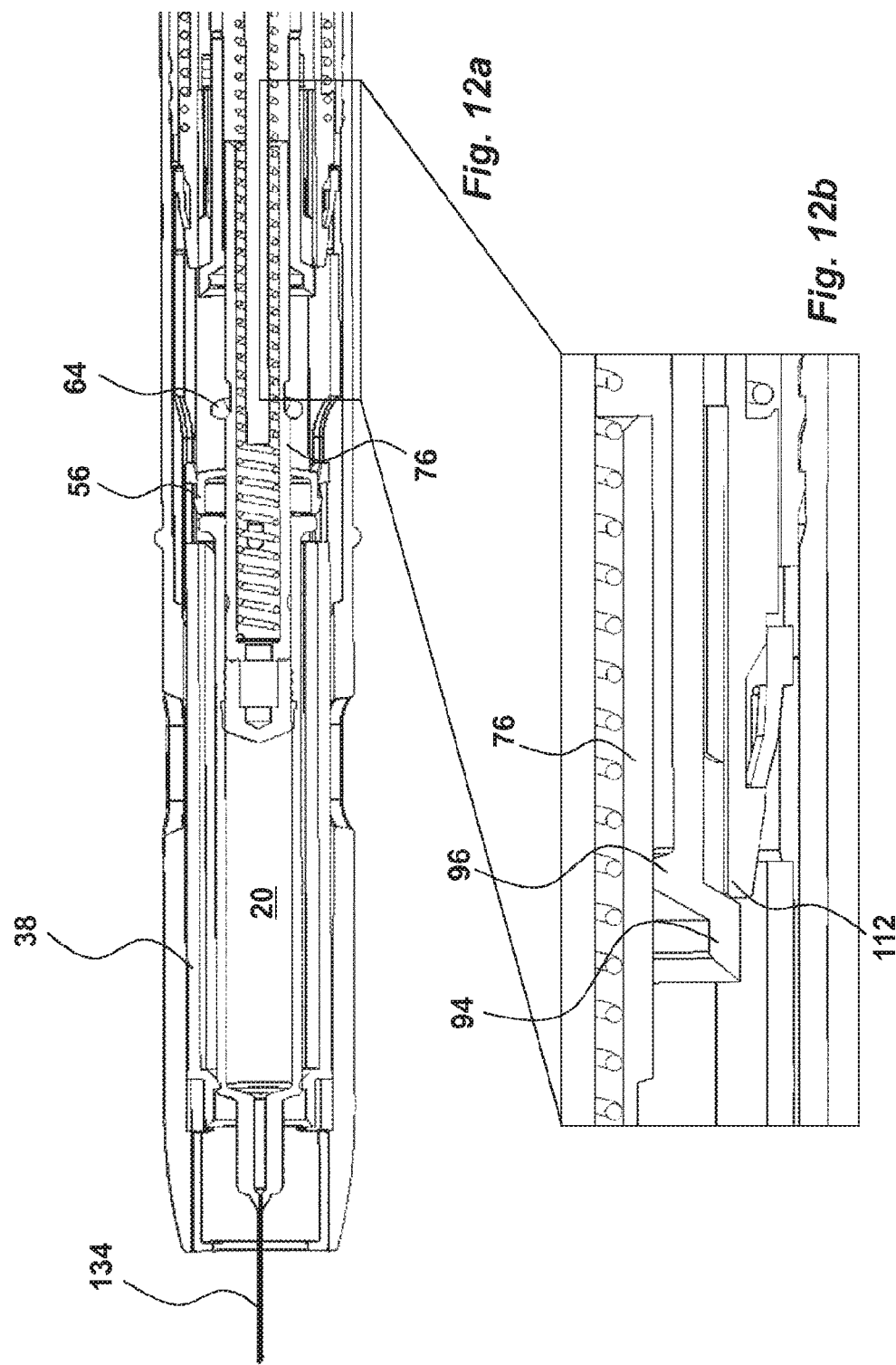

The force of the compression spring 82 urges the plunger rod 76 to push on the stopper 21 of the medicament container 20. But due to the friction between stopper 21 and the container wall and incompressibility of liquid in the medicament container and the very small flow passage through the medicament delivery member 134, the force will push the medicament container 20 forward together with the container holder 38 and the holding member 56, and thereby the medicament delivery member 134 e.g. a needle will penetrate the skin of the patient, FIG. 12a. Furthermore, the actuator sleeve 112 is held in a longitudinal position by the band-shaped part 94 as seen in FIG. 12b because the tongues 100 of the actuator are flexed outwards. The tongues 100 cannot flex inwards due to the ledges 96 now being in contact with the outer surface of the plunger rod 76.

The penetration stops when the proximally directed stop surfaces 45 of the cut-outs 42 of the container holder 38 abut the ledges 32 on the inner surface of the medicament delivery member cover 22 stopping the movement of the container holder 38, the medicament container 20 and the holding member 56. The force from the compression spring 82 now moves the plunger rod 76 and thereby the stopper 21 in the proximal direction inside the medicament container 20 and the liquid medicament is delivered into the patient.

Figure 13:
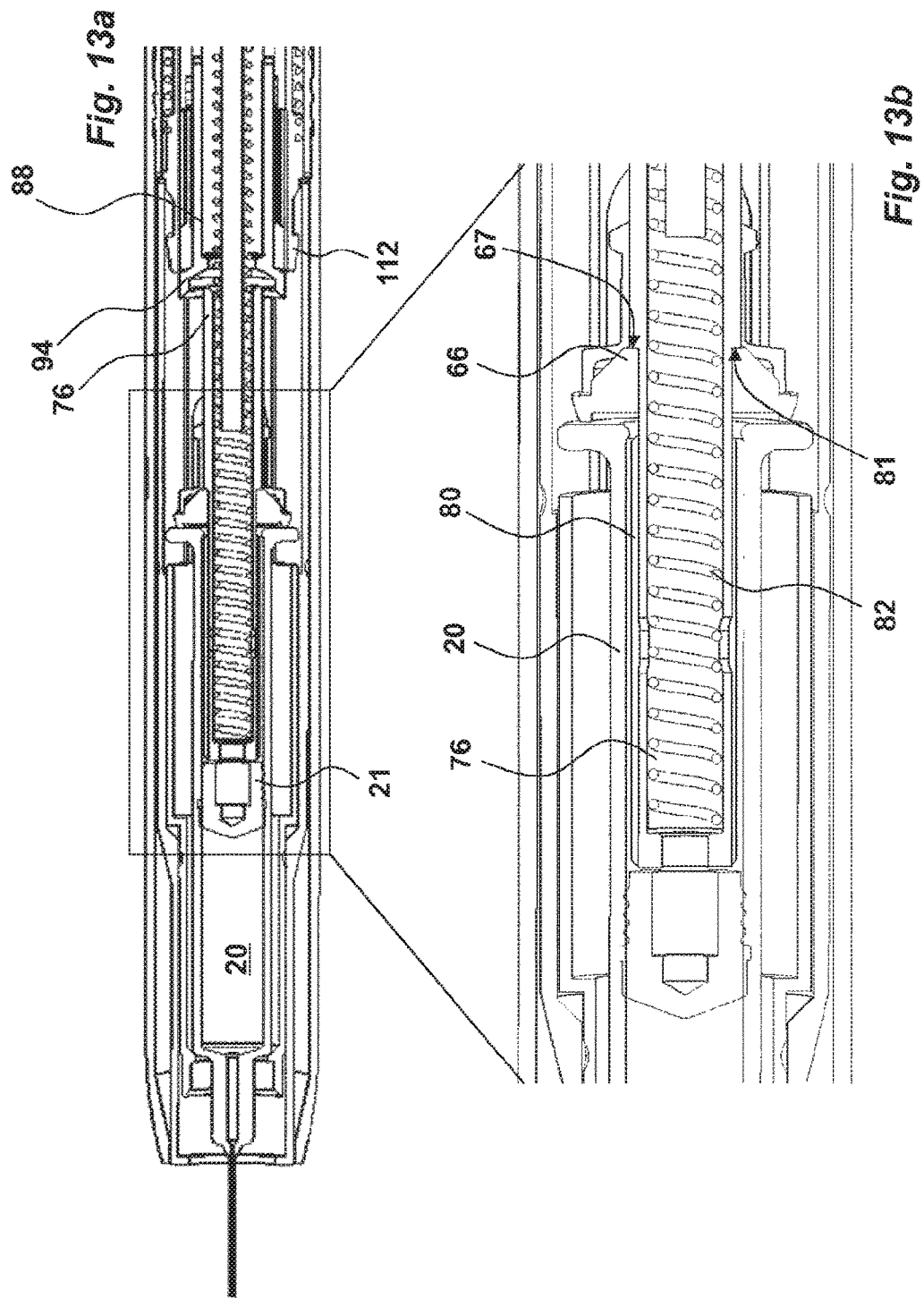
Figure 14:
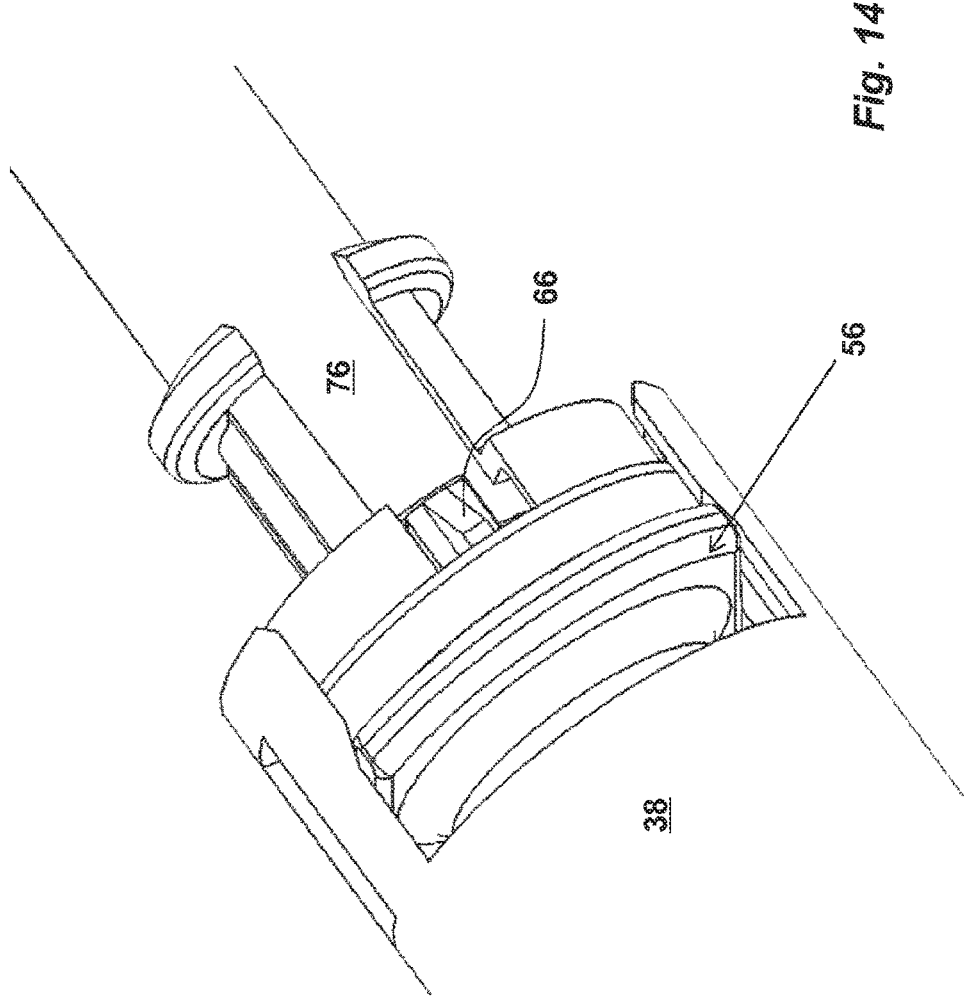

The movement of the plunger rod 76 also causes the distally directed stop protrusions 67 of the holding member 56 to slide in the grooves 80 of the plunger rod 76. The delivery then stops when the stop surfaces of the distally directed stop protrusion 67 reach the proximally directed stop surfaces 81 of the grooves 80, effectively stopping the movement of the plunger rod 76, FIGS. 13 and 14. As seen in FIG. 13a, the plunger rod has stopped well before the stopper 21 has reached a proximal end of the medicament container body. It is thus to be understood that the length X as described may be altered depending on the intended amount of medicament to be delivered into a patient. The device can thus utilize different plunger rods with different lengths of the grooves in order to change the volume of medicament to be delivered. The rest of the components may then not have to be altered or modified in order to change the volumes.

Figure 15:
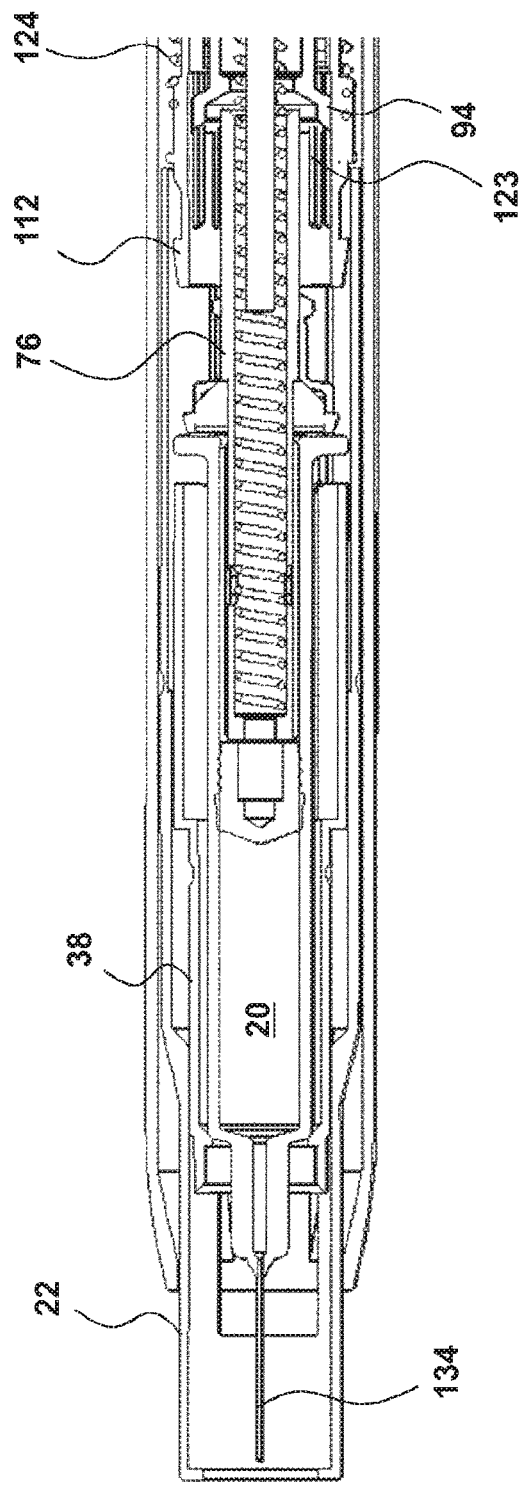

When the plunger rod 76 has moved this distance, its distal end has passed the ledges 96 of the actuator and the tongues 100 are now free to move inwards, FIG. 15. This also releases the actuator sleeve 112 and since the medicament delivery member cover spring 124 is acting on the actuator sleeve 112, it is urged in the proximal direction. When the device is removed from the delivery site, the force of the medicament delivery member cover spring 124 pushes the actuator sleeve 112. Thus, the medicament delivery member cover 22 connected to it in the proximal direction, whereby the medicament delivery member cover 22 is pushed out of the proximal end of the device, surrounds the medicament delivery member 134. The movement of the actuator sleeve 112 causes the band-shaped part 94 of the actuator 88 to pass the ribs 123 on the inner surface of the actuator sleeve 112, FIG. 15. These ribs 123 prevent any attempts to push the medicament delivery member cover 22 back into the device as the ribs 123 will abut the front end of the band-shaped part 94 of the actuator 88. The medicament delivery member cover 22 is thus locked, which prevents unintentional needle sticks.

It is to be understood that the embodiment described above and shown in the drawings is to be regarded only as a non-limiting example of the invention and that it may be modified in many ways within the scope of the patent claims.

The invention claimed is:

1. A medicament delivery device comprising a housing, which housing is arranged to accommodate a container holder with a medicament container, which medicament container comprises a medicament delivery member;
   a power unit interactively connected to the housing comprises a force element and a plunger rod which is arranged to, upon activation, move linearly in a proximal direction and act on a stopper of said medicament container for expelling a dose of medicament through said medicament delivery member;
   a holding member connected to said power unit and to said container holder, the holding member comprising a ring-shaped body comprising an annular ledge arranged around a circumference of the ring-shaped body;
   wherein the annular ledge of the holding member is arranged and shaped to fit into a circumferential groove of the plunger rod for connecting the holding member to the power unit;
   wherein said plunger rod comprises at least one first guide-and-stop element configured to interact with at least one second guide-and-stop element extending radially inwardly from said annular ledge of said holding member for limiting a linear distance the plunger rod is capable of moving in the proximal direction during expelling of medicament, wherein the linear distance corresponds to a dose volume;
   wherein the at least one first guide-and-stop element comprises a proximally directed stop surface and the at least one second guide-and-stop element comprises a distally directed stop protrusion with a stop surface,
   the proximally directed stop surface and the stop surface of the distally directed stop protrusion configured such that movement of the plunger rod in the proximal direction stops when the stop surface of the distally directed stop protrusion reaches the proximally directed stop surface, and
   wherein movement of the plunger rod in the proximal direction is stopped before the stopper has reached a proximal end of the medicament container.

2. The medicament delivery device according to claim 1, wherein the at least one first guide-and-stop element is a longitudinally extending groove having the proximally directed stop surface and wherein the at least one second guide-and-stop element is a radially inwardly positioned stop protrusion having the distally directed stop protrusion with the stop surface.

3. The medicament delivery device according to claim 2, wherein said at least one longitudinally extending groove has a length which is selected based on a required dose volume to be delivered.

4. The medicament delivery device according to claim 1, wherein the annular ledge is configured to interact with inwardly inclined tongues on distally directed tongues of the container holder for connecting the holding member to the container holder.

5. The medicament delivery device according to claim 1, wherein said power unit further comprises an actuator partially surrounding the plunger rod, an actuator sleeve coaxially and slidably arranged on the actuator, a compression spring arranged between the actuator sleeve and the housing and a push button connected to the actuator.

6. The medicament delivery device according to claim 5, wherein the actuator comprises flexible tongues with inclined transition surfaces which meets with a band-shaped part with enlarged diameter and an annular inwardly directed ledge which fit into the circumferential groove of the plunger rod together with the annular ledge of the holding member, at least one stop ledges directed radially outwards from its outer surface, and an attachment post for the push button.

7. The medicament delivery device according to claim 6, wherein the actuator sleeve comprises a front end with a conical part ending in a ledge on its outer surface, a first annular ring, a second annular ring, two oppositely arranged cut-outs configured to accommodate the at least one stop ledges.

8. The medicament delivery device according to claim 7, wherein it further comprises a medicament delivery member cover arranged slidable in relation to said housing and operably connected to said power unit through flexible tongues that pass the annular ledge of the actuator sleeve.

9. The medicament delivery device according to claim 8, wherein the container holder is arranged inside and coaxial with the medicament delivery member cover.

* * * * *